US005670529A

United States Patent [19]
Clarke

[11] Patent Number: 5,670,529
[45] Date of Patent: Sep. 23, 1997

[54] AVOIDANCE OF PRECIPITATION IN 3-ISOTHIAZOLONE FORMULATIONS

[75] Inventor: Philippa Clarke, Co. Durham, England

[73] Assignee: Rohm and Haas Company, Philadelphia, Pa.

[21] Appl. No.: 658,789

[22] Filed: Jun. 5, 1996

[51] Int. Cl.⁶ .................... C07D 231/04; C07D 275/02
[52] U.S. Cl. .................... 514/360; 514/372; 548/213
[58] Field of Search ...................... 514/360, 372; 548/213

[56] References Cited

U.S. PATENT DOCUMENTS

| 3,870,795 | 3/1975 | Miller et al. | 424/270 |
| 5,073,582 | 12/1991 | LeSota et al. | 524/44 |

FOREIGN PATENT DOCUMENTS 2-304005  12/1990  Japan.

Primary Examiner—Johann Richter
Assistant Examiner—Jane C. Osweckі
Attorney, Agent, or Firm—Julie J. L. Cheng

[57] ABSTRACT

Compositions comprising optionally substituted 3-isothiazolone derivative compounds, a metal nitrate, cupric ($Cu^{2+}$) ion in ppm amounts in the form of an inorganic copper salt and water are described for preventing the formation of unsightly precipitations in these compositions during storage.

16 Claims, No Drawings

AVOIDANCE OF PRECIPITATION IN 3-ISOTHIAZOLONE FORMULATIONS

BACKGROUND OF THE INVENTION

This invention relates to the avoidance of precipitation in 3-isothiazolone solutions.

3-isothiazolone compounds (hereafter "active ingredient" or AI) are a very important class of microbicides. Several species have been commercialized and are widely used to inhibit the growth of bacteria, fungi and algae. Among the most important isothiazolones are 2-methyl-3-isothiazolone ("MI") 5-chloro-2-methyl-3-isothiazolone ("CMI"), and especially mixtures thereof. A 3/1 weight ratio mixture of CMI and MI is used in a wide variety of commercial applications around the world. CMI is naturally unstable and much research has been devoted to stabilizing it: without the presence of a stabilizer, a microbicide containing CMI stead fly loses microbiocidal efficacy as the CMI decomposes.

U.S. Pat. No. 3,870,795 teaches the stabilization against chemical decomposition of 3-isothiazolone concentrates containing 25 weight percent (wt %) isothiazolone, by addition of metal nitrite or metal nitrate. Today the majority of commercial 3-isothiazolone products are stabilised with metal nitrate, usually magnesium nitrate. Typical products may contain between 1 and 20 wt % isothiazolone and a similar amount of nitrate salt.

Cupric salt ($Cu^{2+}$) is also known as a stabilizer for isothiazolones, normally in conjunction with magnesium nitrate. The cupric salt is conventionally used at a ratio of about 1:10 to AI since relatively small amounts of cupric ion are necessary for effective stabilization. Commercial isothiazolone products are known containing 1.5 wt % isothiazolone, 1.7 wt % magnesium nitrate and 0.15 wt % (i.e. 1500 ppm) copper nitrate. Some products have much lower levels of cupric ion: the Rohm and Haas product KATHON® WTA (KATHON is a registered trade mark of Rohm and Haas Company) contains 1.5 wt % isothiazolone, 1.7 wt % magnesium nitrate, and just 0.015–0.02 wt % (150–200 ppm) of copper nitrate.

Although the use of magnesium nitrate and/or cupric salts as stabilisers enables isothiazolone products to retain their microbicidal activity for considerable periods of time, other forms of decomposition, which do not significantly affect the level of AI in the composition, can cause problems. One of these is the occasional formation of a precipitate in the formulation during storage. The amount of isothiazolone which decomposes to form the precipitate is very small, so the efficacy of the product is barely affected: however the presence of the precipitate gives an undesirable appearance to users of the product, and it is clearly preferable from a commercial point of view to have a product which does not form such precipitates.

JP 02-304005 discloses compositions containing 0.1–15 wt % isothiazolone and 1–5000 ppm of copper ion, as well as nonionic surfactant and organic solvent: there is no nitrate salt present. These compositions are designed for the stabilisation of aqueous dispersions of polymers, where the presence of metal nitrates would lead to problems of "salt shock". The precipitation problem referred to in this document when nitrates are used as stabilisers is the result of general decomposition of the isothiazolone, and is quite different from that discussed above.

SUMMARY OF THE INVENTION

We have discovered that the addition of extremely low levels of copper ion to isothiazolone-containing formulations can substantially reduce or prevent the problem of unsightly precipitation during storage. Accordingly in a first aspect the present invention provides a composition comprising: a) from 0.1 to 20 wt % of a 3-isothiazolone; b) from 0.1 to 25 wt % of a metal nitrate; c) from 1.0 to 100 ppm of cupric ($Cu^{2+}$) ion; and d) a solvent.

A further aspect of the invention provides a method of reducing or preventing the formation of precipitate in a formulation containing from 0.1 to 20 wt % of a 3-isothiazolone and from 0.1 to 25 wt % of a metal nitrate, comprising incorporating therewith from 1 to 100 ppm of $Cu^{2+}$ion, and another aspect of the invention comprises the use of $Cu^{2+}$ ion to reduce or prevent the formation of precipitate in such a formulation.

DETAILED DESCRIPTION OF THE INVENTION

The $Cu^{2+}$ ion is preferably in the form of an inorganic copper salt such as copper nitrate, although other salts such as copper sulphate may be used. Preferred mounts of $Cu^{2+}$ ion are from 1 to 10 ppm, and more preferably from 1 to 5 ppm. Greater amounts of copper ion may be added, but this is not necessary and merely adds to the expense.

Typical levels of 3-isothiazolone in such compositions are between 0.1 and 20 wt %, with levels of nitrate being between 0.1 and 25 wt %. A preferred formulation comprises from 12 to 16 wt % 3-isothiazolone, from 12 to 25 wt % magnesium nitrate, and from 1 to 5 ppm $Cu^{2+}$ ion.

The metal nitrate is preferably magnesium nitrate, whilst the preferred 3-isothiazolone is a 3:1 mixture of 5-chloro-2-methyl-3-isothiazolone and 2-methyl-3-isothiazolone. Other possible 3-isothiazolones are 4,5-dichloro-2-methyl-3-isothiazolone, 2-n-octyl-3-isothiazolone and 4,5-dichloro-2-octyl-3-isothiazolone.

Preferred solvents are water or certain organic solvents. Examples of organic solvents include polyols, such as glycols or alcohols. Certain aliphatic or aromatic hydrocarbons may also be used. Preferred organic solvents are capped polyols.

Although $Cu^{2+}$ salts are known to stabilise isothiazolones against decomposition when added at much higher levels, it was particularly surprising to discover that trace levels could dramatically affect the quite separate problem of unsightly precipitate formation on storage. It is believed that the $Cu^{2+}$ may interfere in a negative manner catalytically with the reaction that results in the precipitate, thereby reducing the formation of precipitate without consuming the copper; hence the need for only extremely low levels.

EXAMPLES

Formulations of isothiazolone and magnesium nitrate were prepared, with and without added copper nitrate. They were evaluated for precipitate formation by storing at 55° C. or 30° C. and noting the number of days before a precipitate was observed. Decomposition is of course more rapid at 55° C., which is a preferred temperature for accelerated stability testing. The composition of each formulation and the results of the precipitate evaluation are given below: five experiments were run, shown in Tables 1 to 5. In each case, the formulation was based in water. All percentages are weight percentages.

TABLE I

|  | A | B | C | D |
|---|---|---|---|---|
| 5-chloro-2-methyl-3-isothiazolone (%) | 10.2 | 10.2 | 10.1 | 10.1 |
| 2-methyl-3-isothiazolone (%) | 4.0 | 4.0 | 3.9 | 3.9 |
| 4,5-dichloro-2-methyl-3-isothiazolone (%) | 0.5 | 0.5 | 0.5 | 0.5 |
| magnesium nitrate (%) | 15.7 | 13.3 | 13.2 | 13.4 |
| magnesium chloride (%) | 10.9 | 10.9 | 10.7 | 10.6 |
| copper nitrate (ppm) | 0 | 0 | 10 | 30 |
| $Cu^{2+}$ (ppm) | 50 | 500+ | 0 | 0 |
| Days free of precipitate at 55° C.* | 21 | 7 | 37+ | 37+ |
| Precipitate after 37 days at 55° C. (ppm) | 50 | 500+ | 0 | 0 |

*The precipitate evaluation was terminated at 37 days.

TABLE 2

|  | A | B | C | D |
|---|---|---|---|---|
| 5-chloro-2-methyl-3-isothiazolone (%) | 10.7 | 10.7 | 10.5 | 10.5 |
| 2-methyl-3-isothiazolone (%) | 3.5 | 3.5 | 3.6 | 3.6 |
| 4,5-dichloro-2-methyl-3-isothiazolone (%) | 0.4 | 0.4 | 0.4 | 0.4 |
| Magnesium nitrate (%) | 16.5 | 13.8 | 12.9 | 13.5 |
| Magnesium chloride (%) | 9.5 | 9.6 | 9.5 | 9.4 |
| Copper nitrate (ppm) | 0 | 0 | 9 | 30 |
| $Cu^{2+}$ (ppm) | 0 | 0 | 3 | 9 |
| Days free of precipitate at 55° C.* | 11 | 7 | 103+ | 103+ |
| Precipitate after 103 days at 55° C. (ppm) | 500+ | 500+ | 0 | 0 |

*The precipitate evaluation was terminated at 103 days.

TABLE 3

|  | A | B | C | D |
|---|---|---|---|---|
| 5-chloro-2-methyl-3-isothiazolone + 2-methyl-3-isothiazolone (%) | 14.1 | 14.1 | 14.1 | 14.1 |
| Magnesium nitrate (%) | 16.9 | 16.9 | 16.9 | 16.9 |
| Copper nitrate (ppm) | 0 | 9 | 24 | 44 |
| $Cu^{2+}$ (ppm) | 0 | 3 | 8 | 15 |
| Days free of precipitate at 55° C.* | 11 | 104+ | 104+ | 104+ |
| Amount of precipitate after 104 days at 55° C. | 500+ | 0 | 0 | 0 |
| Weeks free of precipitate at 30° C. | 12 | 15+ | 15+ | 15+ |
| Amount of precipitate after 12 weeks at 30° C. | 25 | 0 | 0 | 0 |

*The precipitate evaluations were terminated at 104 days (15 weeks).

TABLE 4

|  | A | B | C | D | E |
|---|---|---|---|---|---|
| 5-chloro-2-methyl-3-isothiazolone + 2-methyl-3-isothiazolone (%) | 14.1 | 14.1 | 14.1 | 14.1 | 14.1 |
| Magnesium nitrate (%) | 16.3 | 16.3 | 16.3 | 16.3 | 16.3 |
| Copper nitrate (ppm) | 0 | 0.3 | 1.5 | 3.0 | 8.9 |
| $Cu^{2+}$ (ppm) | 0 | 0.1 | 0.5 | 1.0 | 3.0 |
| Days free of precipitate at 55° C.* | 5 | 7 | 11 | 54+ | 54+ |
| Amount of precipitate after 54 days at 55° C. | 500+ | 500+ | 25 | 0 | 0 |
| Weeks free of precipitate at 30° C. | 4 | 4 | 4 | 8+ | 8+ |
| Amount of precipitate after 8 weeks at 30° C. | 100 | 75 | 0–10 | 0 | 0 |

*The precipitate evaluations were terminated at 54 days (8 weeks).

TABLE 5

|  | A | B | C | D | E |
|---|---|---|---|---|---|
| 5-chloro-2-methyl-3-isothiazolone + 2-methyl-3-isothiazolone (%) | 14.0 | 14.0 | 14.0 | 14.0 | 14.0 |
| Magnesium nitrate (%) | 16.4 | 16.4 | 16.4 | 16.4 | 16.4 |
| Copper nitrate (ppm) | 0 | 1.5 | 2.2 | 3.0 | 3.0 |
| $Cu^{2+}$ (ppm) | 0 | 0.5 | 0.75 | 1.0 | 1.0 |
| Days free of precipitate at 55° C.* | 7 | 7 | 23+ | 23+ | 23+ |
| Amount of precipitate after 23 days at 55° C. | 50 | 0–10 | 0 | 0 | 0 |
| Weeks free of precipitate at 30° C. | 3 | 3+ | 3+ | 3+ | 3+ |
| Amount of precipitate after 3 weeks at 30° C. | 0–10 | 0 | 0 | 0 | 0 |

*The precipitate evaluations were terminated at 23 days (3 weeks).

In addition to the above experiments, commercial KATHON® 886 sold by Rohm and Haas Company, which contains 15.8% 5-chloro-2-methyl-3-isothiazolone plus 2-methyl-3-isothiazolone and 13.9% magnesium nitrate, was evaluated for precipitate formation with added copper nitrate over a longer period. The results are shown in Table 6 below.

TABLE 6

| Expt | $Cu^{2+}$ (ppm) | Test length (days) | Days free of ppt at 55° C. | Precipitate level at test end (ppm) 55° C. | 30° C. |
|---|---|---|---|---|---|
| 1 | 0 | 187 | 11 | 500+ | 150 ± 30 |
|  | 1.0 | 187 | 187 | 0 | 0 |
|  | 0 | 187 | 11 | 500+ | 150 ± 30 |
|  | 1.0 | 187 | 187 | 0 | 0 |
| 3 | 0 | 181 | 181 | 0 | 0 |
|  | 1.0 | 181 | 181 | 0 | 0 |
| 4 | 0 | 181 | 19 | 500+ | 100 ± 5 |
|  | 1.0 | 181 | 181 | 0 | 0 |
| 5 | 0 | 169 | 3 | 500+ | 500 ± 100 |
|  | 1.0 | 169 | 169 | 0 | 0 |
| 6 | 0 | 169 | 14 | 500+ | 500 ± 100 |
|  | 1.0 | 169 | 169 | 0 | 0 |
| 7 | 0 | 159 | 11 | 500+ | 150 ± 30 |
|  | 1.0 | 159 | 159 | 0 | 0 |
| 8 | 0 | 159 | 11 | 500+ | 250 ± 30 |
|  | 1.0 | 159 | 159 | 0 | 0 |
| 9 | 0 | 158 | 7 | 500+ | 250 ± 30 |
|  | 1.0 | 158 | 158 | 0 | 0 |

Although it can be seen in the above Tables that the amount of precipitate formed even when no copper is present is very small, as previously explained it gives an unsightly appearance to the product, which is undesirable for commercial reasons. All the above results demonstrate clearly the effect of very small amounts of copper ion on the formation of precipitate: as little as 1.0 ppm of $Cu^{2+}$ ion can substantially delay or prevent its appearance.

I claim:

1. A composition comprising
   a) from 0.1 to 20 wt % of an optionally substituted 3-isothiazolone;
   b) from 0.1 to 25 wt % of a metal nitrate;
   c) from 1.0 to 100 ppm of cupric ($Cu^{2+}$) ion in the form of an inorganic copper salt; and
   d) water.

2. Composition according to claim 1, wherein the 3-isothiazolone comprises 5-chloro-2-methyl-3-isothiazolone, 2-methyl-3-isothiazolone, 4,5-dichloro-2-methyl-3-isothiazolone, -n-octyl-3-isothiazolone, or 4,5-dichloro-2-octyl-3-isothiazolone.

3. Composition according to claim 2, wherein the 3-isothiazolone comprises a 3:1 mixture of 5-chloro-2-methyl-3-isothiazolone and 2-methyl-3-isothiazolone.

4. Composition according to claim 1, wherein the amount of $Cu^{2+}$ ion is from 1 to 10 ppm.

5. Composition according to claim 4, wherein the 3-isothiazolone comprises 5-chloro-2-methyl-3-isothiazolone, 2-methyl-3-isothiazolone, 4,5-dichloro-2-methyl-3-isothiazolone, 2-n-octyl-3-isothiazolone, or 4,5-dichloro-2-octyl-3-isothiazolone.

6. Composition according to claim 5, wherein the 3-isothiazolone comprises a 3:1 mixture of 5-chloro-2-methyl-3-isothiazolone and 2-methyl-3-isothiazolone.

7. Composition according to claim 4, wherein the amount of $Cu^{2+}$ ion is from 1 to 5 ppm.

8. Composition according to claim 7, wherein the 3-isothiazolone comprises 5-chloro-2-methyl-3-isothiazolone, 2-methyl-3-isothiazolone, 4,5-dichloro-2-methyl-3-isothiazolone, 2-n-octyl-3-isothiazolone, or 4,5-dichloro-2-octyl-3-isothiazolone.

9. Composition according to claim 8, wherein the 3-isothiazolone comprises a 3:1 mixture of 5-chloro-2-methyl-3-isothiazolone and 2-methyl-3-isothiazolone.

10. Composition according to claim 1, wherein the metal nitrate is magnesium nitrate.

11. Composition according to claim 10, wherein the amount of $Cu^{2+}$ ion is from 1 to 10 ppm.

12. Composition according to claim 11, wherein the amount of $Cu^{2+}$ ion is from 1 to 5 ppm.

13. Composition according to claim 1, wherein the $Cu^{2+}$ ion is in the form of copper nitrate or copper sulphate.

14. Composition according to claim 1, comprising from 12 to 16 wt % of 3-isothiazolone, from 12 to 25 wt % of magnesium nitrate, and from 1 to 5 ppm of $Cu^{2+}$ ion.

15. Method of reducing or preventing the formation of precipitate in a formulation containing from 0.1 to 20 wt % of 3-isothiazolone and from 0.1 to 25 wt % of metal nitrate, comprising incorporating therewith from 1 to 100 ppm of $Cu^{2+}$ ion.

16. Method of using $Cu^{2+}$ ion to reduce or prevent the formation of precipitate in a formulation containing from 0.1 to 20 wt % of a 3-isothiazolone and from 0.1 to 25 wt % of a metal nitrate.

* * * * *